US011827581B2

(12) United States Patent
Chen et al.

(10) Patent No.: US 11,827,581 B2
(45) Date of Patent: Nov. 28, 2023

(54) FULL CONTINUOUS-FLOW PREPARATION METHOD OF L-CARNITINE

(71) Applicant: Fudan University, Shanghai (CN)

(72) Inventors: Fener Chen, Shanghai (CN); Minjie Liu, Shanghai (CN); Meifen Jiang, Shanghai (CN); Dang Cheng, Shanghai (CN); Chao Yu, Shanghai (CN); Huashan Huang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/741,112

(22) Filed: May 10, 2022

(65) Prior Publication Data

US 2022/0267253 A1 Aug. 25, 2022

(51) Int. Cl.
*C07C 227/12* (2006.01)
*C07C 227/08* (2006.01)
*B01J 19/00* (2006.01)

(52) U.S. Cl.
CPC ......... *C07C 227/12* (2013.01); *B01J 19/0093* (2013.01); *C07C 227/08* (2013.01); *B01J 2219/0086* (2013.01); *B01J 2219/00867* (2013.01); *B01J 2219/00889* (2013.01)

(58) Field of Classification Search
None
See application file for complete search history.

(56) References Cited

U.S. PATENT DOCUMENTS 4,710,468 A * 12/1987 Sih .......................... C12P 7/62
435/141

FOREIGN PATENT DOCUMENTS

| CN | 1634870 A | 7/2005 |
| CN | 101875616 A | 11/2010 |
| CN | 102633664 B | 5/2014 |
| CN | 113929589 * 1/2022 .......... B01J 19/0013 |
| CN | 114380706 * 4/2022 .......... B01J 19/0093 |

* cited by examiner

*Primary Examiner* — Amy C Bonaparte

(57) ABSTRACT

A full continuous-flow preparation method of L-carnitine, including: mixing chlorine gas and a diketene solution via a first micromixer followed by transportation to a first microchannel reactor for continuous chlorination and esterification reaction to obtain 4-chloroacetoacetate; feeding the 4-chloroacetoacetate and a reductase to a second micromixer and a second microchannel reactor in sequence for continuous catalytic reaction to obtain (R)-4-chloro-3-hydroxybutyrate; simultaneously transporting the (R)-4-chloro-3-hydroxybutyrate and a trimethylamine solution to a third micromixer and a third microchannel reactor for continuous substitution and hydrolysis reaction; and subjecting the reaction mixture to desalination and concentration to obtain the L-carnitine.

9 Claims, 1 Drawing Sheet

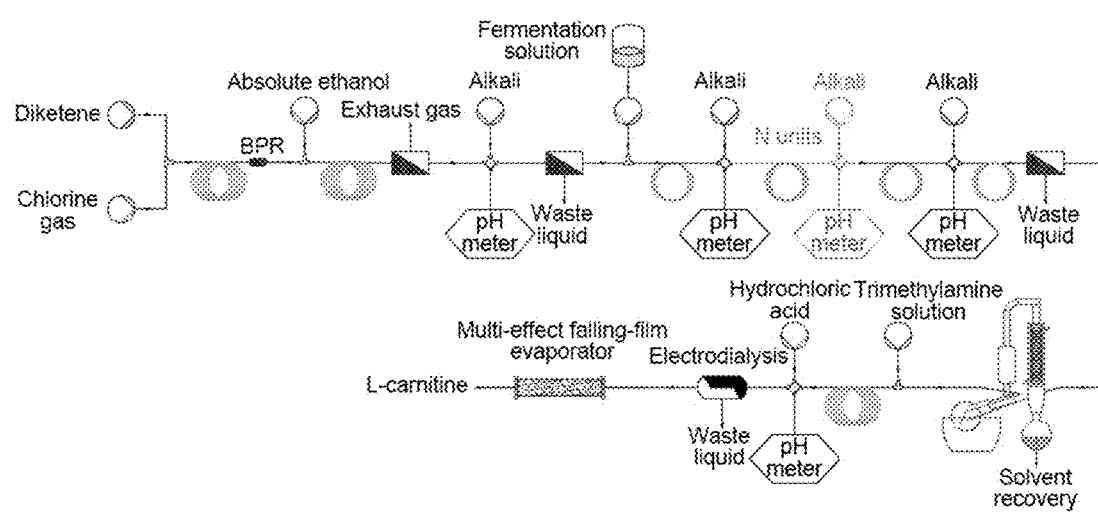

FULL CONTINUOUS-FLOW PREPARATION METHOD OF L-CARNITINE

TECHNICAL FIELD

This application relates to organic chemical engineering, and more particularly to a full continuous-flow preparation method of L-carnitine.

BACKGROUND

L-carnitine is an important naturally-occurring substance shown in formula (1), and has a brilliant application prospect in the preparation of medicines, food additives and feed additives.

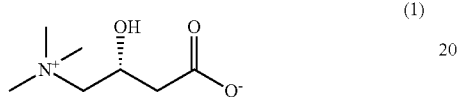
(1)

At present, the L-carnitine is prepared mainly by extraction, biosynthesis and chemical synthesis. Originally, the L-carnitine is extracted from the beef extract, but this approach has numerous and complicated operations and low yield, and thus is not suitable for the large-scale production. The biosynthesis method is mainly performed by converting crotonbetaine into L-carnitine via microbial fermentation or enzymatic catalysis. Unfortunately, the existing biosynthesis strategies still suffer poor conversion rate and troublesome isolation and purification. The chemical synthesis mainly includes two routes. In the first route, the L-carnitine is obtained in the presence of an expensive resolving agent, and this process involves a waste of D-carnitine and low yield (Chinese patent application No. 200410068172.9). With regard to the second synthetic route, the chiral epichlorohydrin or ethyl 4-chloroacetoacetate is used as raw material for synthesis, which requires a highly toxic cyanide or an expensive chiral catalyst (Chinese patent application Nos. 201210089733.8 and 201010198458.4)

Besides, the traditional batch reactor-based synthesis methods also struggle with large time consumption, complicated operation, serious safety hazard, low efficiency and high energy consumption, and thus are not suitable for the large-scale production.

SUMMARY

An objective of this application is to provide a full continuous-flow preparation method of L-carnitine to overcome the defects of large time consumption, serious safety hazard, high energy consumption and low efficiency in the prior art. The preparation method provided herein has shortened reaction time, optimized reaction efficiency, high degree of automation, improved safety and reduced energy consumption, and thus is suitable for the industrial application.

Technical solutions of this application are described as follows.

This application provides a full continuous-flow preparation method of L-carnitine using a micro-reaction system, wherein the micro-reaction system comprises a first micromixer, a first microchannel reactor, a second micromixer, a second microchannel reactor, a third micromixer, a third microchannel reactor, a fourth micromixer and a fourth microchannel reactor communicated in sequence; and the method comprises:

(S1) respectively transporting chlorine gas and a diketene reaction liquid to the first micromixer for mixing, and allowing the reaction mixture in the first micromixer to flow into the first microchannel reactor followed by continuous chlorination reaction;

(S2) transporting the reaction mixture flowing out from the first microchannel reactor and an alcohol solvent into the second micromixer and the second microchannel reactor in sequence for continuous esterification reaction;

(S3) neutralizing the reaction mixture flowing out from the second microchannel reactor with a first alkali followed by continuous extraction and separation to collect a first organic phase; simultaneously transporting the first organic phase and an aqueous solution of a reductase to a third micromixer and a third microchannel reactor for continuous reduction reaction;

(S4) removing the reductase from the reaction mixture flowing out from the third microchannel reactor via an extraction separator followed by continuous extraction and separation to obtain a second organic phase; and concentrating the second organic phase to obtain a concentrated liquid;

(S5) simultaneously transporting the concentrated liquid obtained in step (S4) and a trimethylamine solution to a fourth micromixer and a fourth microchannel reactor in sequence for continuous substitution and hydrolysis reaction; and (S6) neutralizing the reaction mixture flowing out from the fourth microchannel reactor with a second alkali followed by feeding into a demineralization device and a concentration device to obtain the L-carnitine;

as shown in the following reaction scheme:

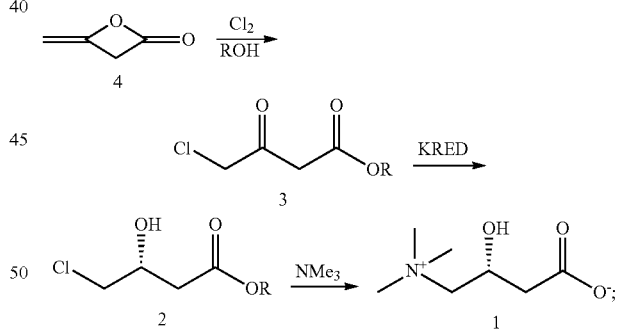

wherein R is $C_1$-$C_6$ alkyl, $C_1$-$C_6$ cycloalkyl or benzyl.

In an embodiment, the diketene reaction liquid is a solution of diketene in an organic solvent; the organic solvent is selected from the group consisting of benzene, methylbenzene, an ester solvent, a chlorinated hydrocarbon solvent and an alkane solvent, preferably methylbenzene or dichloromethane; and the alcohol solvent is selected from the group consisting of $C_1$-$C_6$ alkyl alcohol, $C_1$-$C_6$ cycloalkyl alcohol and benzyl alcohol, preferably methanol or ethanol;

the reductase is a carbonyl reductase. In this embodiment, the reductase is a carbonyl reductase genetically-engineered whole cell; and the trimethylamine solution is a trimethylamine aqueous solution or a trimethylamine alcoholic solution, preferably a trimethylamine aqueous solution.

In an embodiment, in step (S1), the first microchannel reactor is a tubular microchannel reactor, a plate-type microchannel reactor, or other commercially available microchannel reactors.

In an embodiment, in step (S1), a flow ratio of the chlorine gas to the diketene reaction liquid is controlled such that a molar ratio of diketene to the chlorine gas is 1:(0.9~1.5), preferably 1:(1.0~1.2); the first micromixer and the first microchannel reactor are both controlled at −20~50° C., preferably 0-20° C.; a residence time of the reaction mixture in the first microchannel reactor is 0.1-30 min, preferably 0.5-1 min; and a back pressure during the continuous chlorination reaction is controlled to 0.1~1.0 MPa, preferably 0.2~0.5 MPa.

In an embodiment, in step (S2), the alcohol solvent is ethanol; a flow ratio of the reaction mixture obtained in step (S1) to the ethanol is controlled such that a molar ratio of diketene to ethanol is 1:(0.9~1.5), preferably 1:(1.0~1.2); the second micromixer and the second microchannel reactor are both controlled at 20-80° C., preferably 30-50° C.; a residence time of the reaction mixture in the second microchannel reactor is 0.1-30 min, preferably 5-10 min; and a back pressure during the continuous esterification reaction is controlled to 0.1-1.0 MPa, preferably 0.2-0.5 MPa.

In an embodiment, in step (S3), the third micromixer and the third microchannel reactor are both controlled at 20-50° C., preferably 30-40° C.; a residence time of the reaction mixture in the third microchannel reactor is 1-30 min, preferably 10-15 min, and a back pressure during the continuous reduction reaction is controlled to 0.1-1.0 MPa, preferably 0.2-0.5 MPa.

In an embodiment, in step (S5), a flow ratio of the concentrated liquid obtained in step (S4) to the trimethylamine solution is controlled such that a molar ratio of diketene to trimethylamine is 1:(1.0~2.0), preferably 1:(1.0~1.5); the fourth micromixer and the fourth microchannel reactor are both controlled at 20-50° C., preferably 30-40° C.; a residence time of the reaction mixture in the fourth microchannel reactor is 1-30 min, preferably 10-15 min; and a back pressure during the continuous substitution and hydrolysis reaction is 0.1-1.0 MPa, preferably 0.2-0.3 MPa.

In an embodiment, the first micromixer, the second micromixer, the third micromixer and the fourth micromixer are each independently selected from the group consisting of static mixer, T-type micromixer, Y-type micromixer, cross-type mixer, coaxial flow micromixer and flow-focusing micromixer, preferably the cross-type mixer, coaxial flow micromixer or flow-focusing micromixer.

In an embodiment, the first microchannel reactor, the second microchannel reactor, the third microchannel reactor and the fourth microchannel reactor are each independently selected from the group consisting of tubular microchannel reactor, plate-type microchannel reactor, and other commercially available microchannel reactors.

In an embodiment, an inner diameter of the tubular microchannel reactor is 50 μm-10 μmm, preferably 100 μm-5 mm; the plate-type microchannel reactor comprises a first heat exchange layer, a reaction layer and a second heat exchange layer arranged in sequence from top to bottom; the reaction layer is provided with a reaction fluid channel; and a hydraulic diameter of the reaction fluid channel is 50 μm-10 mm, preferably 100 μm-5 mm.

In an embodiment, the continuous extraction separator is a plate-type microchannel extraction separator, a membrane extraction separator, an annular centrifugal extraction separator, a ceramic membrane separator, an electrodialysis device, a continuous concentration device, or a multi-effect falling-film evaporator.

In an embodiment, the plate-type microchannel extraction separator has an inner diameter of 100 μm-10 mm, and comprises a mixing layer and a separation layer; the membrane extraction separator has a hydrophobic membrane with a pore size of 0.1-4 μm; and the annular centrifugal extraction separator has a diameter of 10 cm-1 m, and one or more annular centrifugal extraction separators are connected in series to form an extraction-separation unit.

The full continuous-flow preparation method of L-carnitine using a micro-reaction system provided herein can realize the industrial large-scale production of L-carnitine through a multi-channel parallel amplification strategy.

Compared with the prior art, this application has the following beneficial effects. In the method provided herein for preparing L-carnitine, a full continuous-flow micro-reaction system including a micromixer, a microchannel reactor and a continuous extraction separator communicated in sequence is adopted. Compared with the traditional batch reactor-based synthesis, this application has the following beneficial effects.

1. The full continuous-flow microchannel reaction system has excellent mass transfer, heat transfer and mixing performances, significantly shortening the reaction time from several days (required by the traditional batch reactor) to about 30 min and improving the reaction efficiency. Moreover, the L-carnitine prepared thereby has superior quality and property.
2. By means of the micro-reaction system, the consumption of chlorine gas can be precisely controlled to allow the complete and quantitative conversion of chlorine gas in the microchannel reactor and the safe operation, and prevent the system from being corroded by the excessive gas.
3. The preparation method provided herein achieves the continuous synthesis of L-carnitine in the absence of external intervention, and has high degree of automation, great time and space efficiency, reduced labor intensity and lowered production costs.
4. The preparation method provided herein can be applied to the industrial production through the multi-channel parallel amplification strategy.

BRIEF DESCRIPTION OF THE DRAWINGS

This FIGURE is a flow chart of a full continuous-flow preparation of L-carnitine according to an example of the present disclosure.

DETAILED DESCRIPTION OF EMBODIMENTS

In order to clearly explain the technical solutions, structural features, objectives and advantages of the technical solutions, the disclosure will be described in detail below with reference to the embodiments and accompanying drawings. It should be understood that the embodiments are merely illustrative, and are not intended to limit the scope of the disclosure.

This application will be described in detail below with reference to the embodiments to make the objectives, technical solutions, and advantages of this application clearer.

EXAMPLE 1

The flow chart of the full continuous-flow preparation of L-carnitine was shown in the FIGURE.

Chlorine gas and a solution of diketene in dichloromethane were simultaneously fed to a Protrix microchannel reactor (Chemtrix BV, Protrix) (reaction volume: 4.2 mL; and microchannel diameter: 2 mm), where a flow ratio of the diketene solution to chlorine gas was adjusted to allow a molar ratio of diketene to chlorine to be 1:1.15; a back pressure value of a back pressure valve was set to 0.2 MPa; the Protrix microchannel reactor was controlled at 10° C. 30 seconds later (namely, a residence time of a reaction mixture in the Protrix microchannel reactor was 30 seconds), the reaction mixture was allowed to flow out from an outlet of the Protrix microchannel reactor to enter a gas-liquid separator, so as to remove gas components. The remaining reaction mixture was collected to a buffer tank, and sampled for detecting the conversion rate of diketene. A 100% conversion of diketene was confirmed. Then the reaction mixture in the buffer tank and ethanol were fed to a first T-type micromixer for mixing, where flow rates of the two feeding pumps were adjusted to allow a molar ratio of diketene to ethanol to be 1:1.05; and the first T-type micromixer was controlled at 25° C. The reaction mixture was subsequently transported to a tubular microchannel reactor (10 m in length and 0.8 mm in inner diameter), where a back pressure value of the back pressure valve was set to 0.3 MPa; and the first tubular microchannel reactor was controlled at 50° C. After reacted for 5 minutes (namely, a residence time of the reaction mixture in the first tubular microchannel reactor was 5 minutes), the reaction mixture was allowed to flow out from an outlet of the first tubular microchannel reactor and transported with a saturated sodium bicarbonate solution to a second T-type micromixer with a temperature controlled at 25° C. After that, the reaction mixture was continuously transported to a first continuous extraction separator, and at the same time, a dichloromethane solvent was fed as an extractant from another inlet into the first continuous extraction separator with a temperature therein controlled at 25° C. After 1 min (namely, a residence time of the reaction mixture in the first continuous extraction separator was 1 min), an organic phase containing a compound (3) was collected from a heavy phase outlet of the first continuous extraction separator, and an aqueous phase was discharged from a light phase outlet.

The obtained organic phase and a reductase aqueous solution were delivered to a third T-type micromixer for mixing, and the reaction mixture was fed to a plurality of series-connected second tubular microchannel reactors (2 m in length of a single tube and inner diameter in 0.8 mm) with pH adjustment and reacted for 15 min (namely, a residence time of the reaction mixture in the tubular microchannels was 15 min), where the back pressure value of the back pressure valve was set to 0.2 MPa, and the second tubular microchannel reactors were controlled at 30° C. The reaction mixture was sampled for detecting a conversion rate of the compound (3), and the results demonstrates the complete conversion of the compound (3). The reaction mixture was allowed to flow out from an outlet of the microchannel reactors, pass through a ceramic membrane separator to remove the reductase and enter a second continuous extraction separator, where an aqueous phase was discarded, and an organic phase was collected and treated via a continuous concentration device to remove dichloromethane, so as to obtain a compound (2).

The obtained compound (2) and a trimethylamine aqueous solution were fed to a fourth T-type micromixer for mixing, and then sent to a third tubular microchannel reactor (10 m in length and 0.8 mm in inner diameter), where flow rates of the two feeding pumps were adjusted such that a molar ratio of diketene to trimethylamine was 1:1.3; a back pressure value of the back pressure valve was set to 0.3 MPa, and the third tubular microchannel reactor was controlled at 25° C. After reacted for 10 min (namely, a residence time of the reaction mixture in the third tubular microchannel reactor was 10 min), the reaction mixture was sampled for detecting a conversion rate of the compound (2). The results confirmed that the compound (2) experienced a complete conversion. The reaction mixture was allowed to flow out from an outlet of the third tubular microchannel reactor, and fed to a fifth T-type micromixer with a dilute hydrochloric acid solution, where the fifth T-type micromixer was set to 25° C. Then the reaction mixture was transported to an electrodialysis device for desalination, and a multi-effect falling-film evaporator for concentration, and subjected to crystallization to obtain a white solid L-carnitine with a purity of 99% (65% yield calculated by diketene).

EXAMPLE 2

Example 2 was basically the same as the Example 1, except that the micromixer used herein was a Y-type micromixer. In this embodiment, the substrate diketene experienced a complete conversion, and the target product L-carnitine had a total yield of 63% and a purity of 99%.

EXAMPLE 3

Example 3 was basically the same as the Example 1, except that the microchannel reactor used herein for chlorination reaction was a tubular microchannel reactor with a volume of 10 mL and an inner diameter of 0.8 mm. In this embodiment, the substrate diketene experienced a complete conversion, and the target product L-carnitine had a total yield of 60% and a purity of 99%.

EXAMPLE 4

Example 4 was basically the same as the Example 1, except that the back pressure adopted herein was 0.5 MPa. In this embodiment, the substrate diketene experienced a complete conversion, and the target product L-carnitine had a total yield of 60% and a purity of 99%.

EXAMPLE 5

Example 5 was basically the same as the Example 1, except that the molar ratio of diketene to chlorine gas was 1:1.3. In this embodiment, the substrate diketene experienced a complete conversion, and the target product L-carnitine had a total yield of 55% and a purity of 99%.

EXAMPLE 6

Example 6 was basically the same as the Example 1, except that the molar ratio of diketene to ethanol was 1:1.2. In this embodiment, the substrate diketene experienced a complete conversion, and the target product L-carnitine had a total yield of 63% and a purity of 99%.

EXAMPLE 7

Example 7 was basically the same as the Example 1, except that the molar ratio of diketene to trimethylamine was 1:1.5. In this embodiment, the substrate diketene experienced a complete conversion, and the target product L-carnitine had a total yield of 65% and a purity of 99%.

It should be noted that the embodiments are merely illustrative, and are not intended to limit the scope of the application. It should be understood that any changes, improvements and modifications made by those skilled in the art without departing from the spirit shall fall within the scope of the present application defined by the appended claims.

What is claimed is:

1. A full continuous-flow preparation method of L-carnitine using a micro-reaction system, the micro-reaction system comprising a first micromixer, a first microchannel reactor, a second micromixer, a second microchannel reactor, a third micromixer, a third microchannel reactor, a fourth micromixer and a fourth microchannel reactor communicated in sequence; and the method comprising:
   (S1) respectively transporting chlorine gas and a diketene reaction liquid to the first micromixer for mixing, and allowing the reaction mixture in the first micromixer to flow into the first microchannel reactor followed by a continuous chlorination reaction;
   (S2) transporting the reaction mixture flowing out from the first microchannel reactor and an alcohol solvent into the second micromixer and the second microchannel reactor in sequence fora continuous esterification reaction;
   (S3) neutralizing the reaction mixture flowing out from the second microchannel reactor with a first alkali followed by a continuous extraction and separation to collect a first organic phase; simultaneously transporting the first organic phase and an aqueous solution of a reductase to the third micromixer and the third microchannel reactor fora continuous reduction reaction;
   (S4) removing the reductase from the reaction mixture flowing out from the third microchannel reactor via an extraction separator followed by a continuous extraction and separation to obtain a second organic phase; and concentrating the second organic phase to obtain a concentrated liquid;
   (S5) simultaneously transporting the concentrated liquid obtained in step (S4) and a trimethylamine solution to the fourth micromixer and the fourth microchannel reactor in sequence fora continuous substitution and hydrolysis reaction; and
   (S6) neutralizing the reaction mixture flowing out from the fourth microchannel reactor with a second alkali followed by feeding the neutralized reaction mixture into a demineralization device and a concentration device to obtain the L-carnitine.

2. The full continuous-flow preparation method of claim 1, wherein the diketene reaction liquid is a solution of diketene in an organic solvent; the organic solvent is selected from the group consisting of benzene, methylbenzene, an ester solvent, a chlorinated hydrocarbon solvent and an alkane solvent;
   the reductase is a carbonyl reductase; and
   the trimethylamine solution is a trimethylamine aqueous solution or a trimethylamine alcoholic solution.

3. The full continuous-flow preparation method of claim 1, wherein in step (S1), a flow ratio of the chlorine gas to the diketene reaction liquid is controlled such that a molar ratio of diketene to the chlorine gas is 1:0.9-1.5;
   the first micromixer and the first microchannel reactor are both controlled at −20~50° C.; a residence time of the reaction mixture in the first microchannel reactor is 0.1~30 min; and a back pressure during the continuous chlorination reaction is controlled to 0.1~1.0 MPa.

4. The full continuous-flow preparation method of claim 1, wherein in step (S2), the alcohol solvent is ethanol; a flow ratio of the reaction mixture obtained in step (S1) to ethanol is controlled such that a molar ratio of initial diketene to ethanol is 1:0.9-1.5; the second micromixer and the second microchannel reactor are both controlled at 20-80° C.; a residence time of the reaction mixture in the second microchannel reactor is 0.1-30 min; and a back pressure during the continuous esterification reaction is controlled to 0.1-1.0 MPa.

5. The full continuous-flow preparation method of claim 1, wherein in step (S3), the third micromixer and the third microchannel reactor are both controlled at 20-50° C.; a residence time of the reaction mixture in the third microchannel reactor is 1-30 min; and a back pressure during the continuous reduction reaction is controlled to 0.1-1.0 MPa.

6. The full continuous-flow preparation method of claim 1, wherein in step (S5), a flow ratio of the concentrated liquid obtained in step (S4) to the trimethylamine solution is controlled such that a molar ratio of initial diketene to trimethylamine is 1:1.0-2.0; the fourth micromixer and the fourth microchannel reactor are both controlled at 20-50° C.; a residence time of the reaction mixture in the fourth microchannel reactor is 1-30 min; and a back pressure during the continuous substitution and hydrolysis reaction is 0.1-1.0 MPa.

7. The full continuous-flow preparation method of claim 1, wherein the first micromixer, the second micromixer, the third micromixer and the fourth micromixer are each independently selected from the group consisting of static mixer, T-type micromixer, Y-type micromixer, cross-type mixer, coaxial flow micromixer and flow-focusing micromixer; and the first microchannel reactor, the second microchannel reactor, the third microchannel reactor and the fourth microchannel reactor are each independently a tubular microchannel reactor, a plate-type microchannel reactor, or other commercially available microchannel reactors.

8. The full continuous-flow preparation method of claim 7, wherein an inner diameter of the tubular microchannel reactor is 50 μm-10 mm; the plate-type microchannel reactor comprises a first heat exchange layer, a reaction layer and a second heat exchange layer arranged in sequence from top to bottom; the reaction layer is provided with a reaction fluid channel; and a hydraulic diameter of the reaction fluid channel is 50 μm-10 mm.

9. The full continuous-flow preparation method of claim 1, wherein the continuous extraction separator is a plate-type microchannel extraction separator, a membrane extraction separator, an annular centrifugal extraction separator, a ceramic membrane separator, an electrodialysis device, a continuous concentration device, or a multi-effect falling-film evaporator.

* * * * *